(12) United States Patent
van Neer et al.

(10) Patent No.: US 10,073,063 B2
(45) Date of Patent: Sep. 11, 2018

(54) ULTRASONIC PIPELINE INSPECTION SYSTEM AND METHOD

(71) Applicant: Nederlandse Organisatie voor toegepast-natuurwetenschappelijk onderzoek TNO, The Hague (NL)

(72) Inventors: Paul Louis Maria Joseph van Neer, The Hague (NL); Gerrit Blacquiere, The Hague (NL); Arno Willem Frederik Volker, The Hague (NL); Huibert Blokland, The Hague (NL)

(73) Assignee: NEDERLANDSE ORGANISATIE VOOR TOEGEPAST-NATUURWETENSCHAPPELIJK ONDERZOEK TNO (NL)

( * ) Notice: Subject to any disclaimer, the term of this patent is extended or adjusted under 35 U.S.C. 154(b) by 108 days.

(21) Appl. No.: 15/105,907

(22) PCT Filed: Dec. 19, 2014

(86) PCT No.: PCT/NL2014/050887
§ 371 (c)(1),
(2) Date: Jun. 17, 2016

(87) PCT Pub. No.: WO2015/093960
PCT Pub. Date: Jun. 25, 2015

(65) Prior Publication Data
US 2016/0320346 A1 Nov. 3, 2016

(30) Foreign Application Priority Data
Dec. 20, 2013 (EP) .................................... 13199153

(51) Int. Cl.
*G01N 29/07* (2006.01)
*G01N 29/04* (2006.01)
(Continued)

(52) U.S. Cl.
CPC ........... *G01N 29/07* (2013.01); *G01N 29/043* (2013.01); *G01N 29/262* (2013.01); *G01N 29/46* (2013.01);
(Continued)

(58) Field of Classification Search
CPC .... G01N 29/07; G01N 29/043; G01N 29/262; G01N 29/46; G01N 29/11; G01N 29/449; G01N 29/48; G01N 29/341; G01N 29/069
See application file for complete search history.

(56) References Cited

U.S. PATENT DOCUMENTS 4,537,073 A * 8/1985 Ooshiro .................. G01N 29/22
73/602
4,807,484 A * 2/1989 Goedecke ............ G01N 27/902
73/865.8
(Continued)

FOREIGN PATENT DOCUMENTS

FR 1160399 5/2013
WO WO03083466 10/2003

*Primary Examiner* — Helen Kwok
(74) *Attorney, Agent, or Firm* — Hoffmann & Baron, LLP

(57) ABSTRACT

A hollow structure like a pipeline is inspected using an array of ultrasound transmitters located within the hollow structure distributed over different radial directions from a center of the array. Parameters such as ellipticity, defining a shape and/or orientation of an inner surface of a wall of the hollow structure are first determined based on measured delays between transmission of ultrasound pulses from the transmitters to reception of first reflections of those ultrasound pulses. Parameters may be used that define an elliptically shaped cross-section of the inner wall surface for example. Next an ultrasound wavefront composed of joint transmissions from the transmitters along at least a sector of the array is transmitted, using relative time delays between waves transmitted by the respective ones of the transmitters to (Continued)

compensate for estimated differences between travel times from the transmitters to the shape defined by the parameters. Reflections of the joint transmissions are detected. The reflections may be detected by computing derivatives with respect to frequency of phase values of Fourier transforms of the reflected signals and detecting peaks in the size of the computed derivatives of the phase values.

17 Claims, 4 Drawing Sheets

(51) Int. Cl.
    *G01N 29/26*     (2006.01)
    *G01N 29/46*     (2006.01)

(52) U.S. Cl.
    CPC . *G01N 2291/044* (2013.01); *G01N 2291/106* (2013.01); *G01N 2291/2636* (2013.01)

(56) References Cited

U.S. PATENT DOCUMENTS

| | | | | |
|---|---|---|---|---|
| 5,460,046 A * | 10/1995 | Maltby | ............. | G01N 29/09 73/623 |
| 5,641,909 A * | 6/1997 | Kiefer | ............. | G01N 29/0672 73/623 |
| 5,648,613 A * | 7/1997 | Kiefer | ............. | G01N 29/0672 73/609 |
| 6,789,427 B2 * | 9/2004 | Batzinger | ............. | G01N 29/069 73/614 |
| 7,293,461 B1 * | 11/2007 | Girndt | ............. | G01N 29/04 310/336 |
| 7,299,697 B2 * | 11/2007 | Siddu | ............. | G01N 29/0645 73/587 |
| 7,987,724 B2 * | 8/2011 | Takada | ............. | G01N 29/0645 600/447 |
| 8,776,558 B2 * | 7/2014 | Volker | ............. | G01N 29/043 70/39 |
| 9,255,910 B2 * | 2/2016 | Volker | ............. | G01B 17/02 |
| 9,739,752 B2 * | 8/2017 | Hunter | ............. | G01N 29/07 |
| 2003/0136195 A1 * | 7/2003 | Krieg | ............. | G01N 29/07 73/628 |
| 2006/0195273 A1 | 8/2006 | Maurer et al. | | |

* cited by examiner

ULTRASONIC PIPELINE INSPECTION SYSTEM AND METHOD

This application is the U.S. National Phase of, and Applicants claim priority from, International Patent Application Number PCT/NL2014/050887 filed Dec. 19, 2014, which claims priority from EP13199153.1 filed Dec. 20, 2013, each of which is incorporated herein by reference.

FIELD OF THE INVENTION

The invention relates to a method and device for ultrasonic inspection of a pipeline, and more generally a hollow structure, from a space within this structure.

BACKGROUND

Ultrasonic pipeline inspection may be performed using a Pipe Inspection Gage (PIG) provided with an array of ultrasound transducers. During inspection the PIG moves through the pipeline and the ultrasound transducers are used to detect ultrasound reflections from the pipeline wall. When the wavelength is sufficiently shorter than the thickness of the pipeline wall, pulse transmission from the PIG results in distinguishable pulse reflections from the inner and outer surface of the pipeline wall. The reflected pulse from the inner surface arrives first, followed by a reflected pulse from the outer surface, which is much smaller, because most of the wave intensity is reflected by the inner surface.

Travel time difference between reflections from the inner and outer surface can be used to determine wall thickness, enabling detection thickness reduction due to wear and corrosion. Furthermore, defects like cracks in the pipe give rise to additional reflections with different travel times, which can be used to detect such defects.

WO 03/083466 describes an apparatus for inspecting the cement casing of a bore hole, comprising a cylindrical array of ultrasound transducers, which makes it possible to produce directed wave fronts. Casing properties may be detected by measuring the decay rate of waves that resonate between the inner and outer surface of a metal pipe in the borehole, in a direction normal to the casing.

WO 03/083466 mentions the problem that conventional inspection techniques assume that the cylindrical array is centered in the pipe, but that the array may in fact be located eccentrically. It is proposed to apply relative delays to the ultrasound transmitted from different transmitters in order to compensate for the eccentricity, thereby effectively centering the generated circular wave front on the pipe axis. The compensation for eccentricity is designed to provide substantially parallel incident wave fronts on the inner surface of the wall, with minimized phase variation of the incident wave front as a function of circumferential position along the wall in a plane of the array. As a result, the adjusted relative time shift of each transmitter substantially compensates for the deviation between the average travel time from all transmitters and the travel time from that transmitter to a corresponding nearest point on the pipe wall.

During use of a pipeline, deposits may accumulate on the inner surface of the pipeline wall. This is called scaling. In oil pipelines for example, a wax-like deposit is formed, often contaminated with particles like sand and corroded metal scraps. With time, such a deposit becomes effectively impenetrable for ultrasound at the frequencies needed to resolve reflected pulses from the inner and outer surfaces of the pipeline wall. Also bends and other deformations can obstruct inspection.

SUMMARY

Among others, it is an object to provide for a method and system for ultrasound inspection of a hollow structure like a pipeline with scaling inside the structure.

A method is provided for ultrasound inspection of a hollow structure using an array of ultrasound transmitters located within the hollow structure distributed over different radial directions from a center of the array. The hollow structure is mainly cylindrical, with parts wherein a cross section of the structure is substantially the same at different positions along an axial direction, differences between cross sections at different axial positions being due to accidental variations except at bends. The ultrasound transmitters may be ultrasound transducers for example, i.e. transmitters that can also be used as receivers.

The method comprises determining one or more parameters defining a shape and/or orientation of that shape of an inner surface of a wall of the structure based on measured delays, which have been measured between transmission of ultrasound pulses from the transmitters to reception of earliest reflections of those ultrasound pulses. As the one or more parameters represent shape, i.e. not merely size, they allow for anisotropy, or in other words deviation from a circular shape. In a range of possible values of the parameter(s) the shape is anisotropic.

The method furthermore comprises transmitting an ultrasound wave front composed of joint transmissions from the transmitters along at least a sector of the array, with relative time delays between waves transmitted by the respective ones of the transmitters to compensate for estimated differences between travel times from the transmitters to the shape defined by the one or more parameters; and detecting reflections of the joint transmissions.

The method may comprise measuring the delays between transmission and reception of earliest reflections for the parameter determination with the transmitters at the location where the joint transmission will be performed. But instead other measured delays may be used, for example delays measured at adjacent locations reached earlier by the PIG, or a combination of measurements at the location where the joint transmission will be performed and one or more other locations.

To detect defects in the pipeline wall or other structure, on which scaling is present on the inside, measurements at relatively low ultrasound frequencies at less than one Megahertz are more useful than higher frequencies. Measurements of wall properties using ultrasound can be obscured by the excitation of shear waves in the wall. Excitation of shear waves can be avoided when the incident wave front on the wall is parallel to the wall.

The known compensation for eccentric location of the array with respect to the pipe is conventionally made on the implicit assumption that the pipe wall has a circular cross section with the plane wherein the array of transducers is located. However, it has been found that compensation for eccentric location of the array still gives rise to confused measurements due to shear waves, especially in pipelines that have been in use for some time, or when the plane of the array is not oriented perpendicular to the pipe axis and in other structures where the cross-section of the wall itself is not circular.

To reduce this effect, the method uses relative transmission time delays computed according to the criterion to realize a wave front with equal phase as a function of circumferential position on the shape defined by estimated one or more parameters. Use of parameters of the shape is used to prevent that local defects become invisible after compensation. As for the known compensation for eccentricity, the adjusted relative time delays of transmitters at different locations in the array may be selected to compensate substantially for deviations between average travel and travel time from each transmitter in the array to a corresponding nearest points on the pipe wall, but using instead points on the pipe wall defined by the shape and/or orientation parameters that have been determined from reflections. Effectively the relative delays may be selected by determining an inverse of a function that expresses a representation of phase of the incident wave front at a surface defined by the parameters as a function of circumferential position along that surface. The inverse function is computed for a wave front representation with minimal phase variation of the incident wave front as a function of circumferential position at the surface defined by the parameters. In an embodiment, inverse may be computed using a fitting algorithm that determines a set of delays that minimizes a measure of this phase variation, such as a sum or integral of squares of phase deviations between the phase of the wave front as a function of position at the inner surface of the wall on one hand and an average phase at the inner surface of the wall on the other hand.

In exemplary embodiments, the parameters may define an elliptically shaped cross-section of the inner wall surface of a pipeline for example, a polygonal shaped cross-section, and/or a curved shaped cross-section part, the curved shaped cross-section part having ends meeting at an angle described by the parameters. An elliptically shaped cross-section can be used to correct for an inclined orientation of the plane wherein the transmitters are located.

In an embodiment the reflections of the jointly transmitted ultrasound waves are detected by computing derivatives with respect to frequency of phase values of Fourier transforms of the reflected signals and detecting peaks in the size of the computed derivatives of the phase values. This enables the detection of wall thickness in the case of the low frequencies used to work with scaled walls. Preferably peaks in the derivatives of the phase values are used that correspond to dips in the amplitude response, typically due to destructive interference of reflections from the pipe wall.

In an embodiment wall thickness may be determined from a lowest frequency at which a peak has been detected, and/or distance between detected successive peaks at higher frequencies. For inspection it can be determined whether the lowest frequency and/or distance lies within a predetermined range, for example below a threshold defined to distinguish faulty pipe walls from acceptable pipe walls. The described use of adaptable parameters to define the shape and/or orientation of an inner surface makes this type of detection more reliable.

In an embodiment, the reflected signals of the jointly transmitted ultrasound waves are received at an array of receivers, and the reflected signals are time shifted to compensate for estimated differences between travel times to different receiver from the shape defined by the parameters. This makes detection of anti-resonances more reliable. When transducers are used, each transducer may be used as a transmitter as well as as a receiver.

In an embodiment, defects at intermediate locations between the inner and outer surface of a wall of the structure are inspected. Herein reflected signals of the jointly transmitted ultrasound waves are received at an array of receivers, and for each of said intermediate locations the reflected signals are time shifted to compensate for estimated travel time differences to and from the intermediate location, dependent on the shape defined by the parameters. Such a form of processing is known per se as Stolt migration. In the inspection of the wall, this provides for an improved distinction between real defects and ultrasound propagation artifacts.

In an embodiment, the ultrasound pulses used to select the parameters are transmitted simultaneously from the transmitters along at least said sector of the array, and the delays between reception of the transmitted ultrasound pulses are detecting by correlating predetermined reference signals with measured signals received in response to the transmitted ultrasound pulses. This provides for accurate parameter determination. The reference signals may be determined for example by placing the array in a reference structure and recording reflected pulses from that reference structure.

BRIEF DESCRIPTION OF THE DRAWING

These and other objects and advantageous aspects will become apparent from a description of exemplary embodiments with reference to the following figures.

DETAILED DESCRIPTION OF EXEMPLARY EMBODIMENTS

Figure 1:
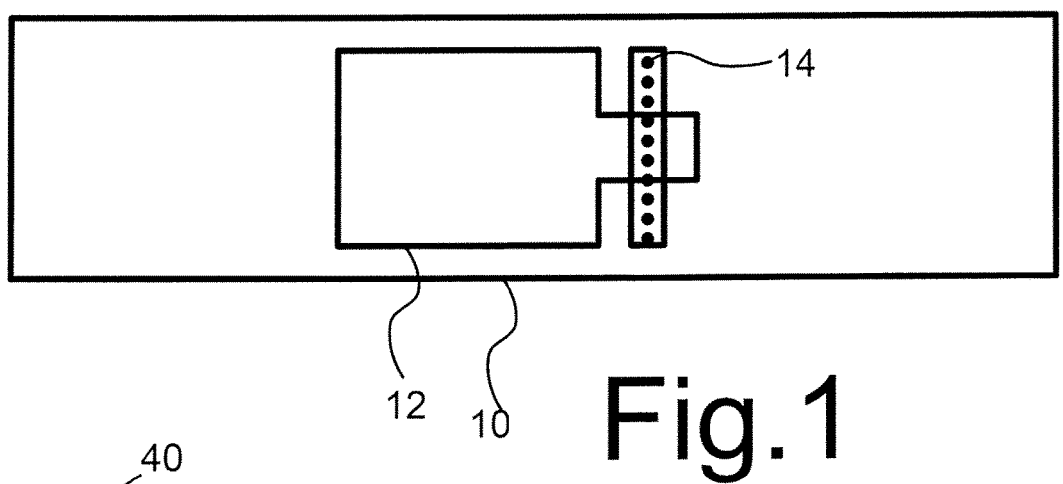
FIG. 1 shows an array of ultrasound transmitters located in a pipe

FIG. 1 shows a pipe 10 in cross-section, with a PIG comprising a ring 12 with an array of ultrasound transducers 14 mounted thereon. Pipe 10 extends in an axial direction perpendicular to the plane of the drawing, as well as a radial direction and a circumferential direction. The PIG may contain spacers (not shown) to support the PIG against the inner surface of pipe 10 at one or more axial positions other than the axial position of the transducers. Preferably, the array comprises at least 50 transducers, located at equidistant circumferential positions at equal radial distances from a central axis of the array, preferably with at most half a wavelength at the highest used frequency (e.g. 1.2 Mhz) between successive transducers, although in practice a slightly higher distance may be used. By way of example, the array may comprise 256 transducers (less shown in the figure). In operation, the transducers are used to transmit ultrasound pulses and detect resulting reflected signals.

Spectral domain measurements at frequencies below 1 MHz make it possible to perform inspection of a scaled pipeline. For each spectral frequency, a spectral domain measurement combines contributions from a plurality of reflection peaks. As an example spectral domain measurements, Fourier transforms $Str(f,m)$ of the time dependent signals $S(t;m)$ for different circumferential positions n may be computed from the time dependent signals $S(t;m)$. Such a Fourier transform $Str(f,m)$ has peaks and/or clips at successive multiples of a basic frequency, which correspond to resonance frequencies of standing waves in the pipe wall between the inner and outer surface and anti-resonances where destructive interference occurs. The expression for these successive frequencies of anti-resonances (indexed by n) is $$f(n)=nC/(2L)$$

(For resonances $f(n)=(n+\frac{1}{2})C/2L$). Herein C is the speed of sound in the pipe wall and L is its thickness. The frequencies $f(n)$ are a multiple of a basic frequency $Fb=C/2L$, which corresponds to an ultrasound standing wave anti-resonance mode with a half period between the inner and outer surface of the pipe wall.

For an example of a practical pipe with about 250 mm diameter, with a wall thickness of 12.7 mm, the basic frequency Fb is about 200 kHz, well below the frequencies at which scaling blocks detection. In fact several multiples of this basic frequency are below the frequencies at which deposits block detection.

The Fourier transform comprises a product of the spectral response function of the deposits that form the scaling and the spectral response function of the pipe wall. The Fourier transform of the received signal is generally a product of factors that includes the Fourier transform of the pulses emitted by transducers 10, the spectral response function of the scaling, the spectral response function of the pipe wall and the spectral response function of the receiving system. The spectral response function of the scaling limits the response to a low pass band up to about 1 Mhz. In principle, as long as the other factors are designed to be less restrictive, or at least include a band that allows the basic frequency Fb to be measured, this makes it possible to estimate pipe wall thickness even in the presence of scaling.

Unfortunately, use of the Fourier transforms $Str(f,m)$ may suffer from a problem when the central axis of the array of transducers 14 is eccentric or not-parallel to the central axis of pipe 10, or when the pipe cross-section shape itself is not circular. Shear waves will then be excited in the pipe wall, which may disturb the signal processing. It has been found that, even for a pipe wall with uniform thickness the frequency of the lowest peak in the Fourier transform may vary as a function of circumferential position. Moreover, the higher frequency peaks may not be evenly spaced. This effect can be reduced by applying circumferential position dependent time shifts to the transmitted signals.

Figure 2:
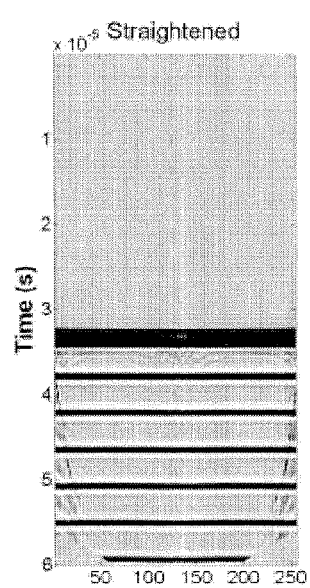
FIG. 2 shows a plot of the detected reflections

FIG. 2 shows a plot of the detected reflections obtained by applying relative time shifts to the transmitted ultrasound signals as a function of circumferential positions, and circumferential position dependent time shifts to the received signals. As can be seen subsequent reflections have substantially position independent time delays. Also the Fourier transformation of the received signals has anti-resonances substantially at circumferential position independent multiples of a basic frequency.

Figure 3:
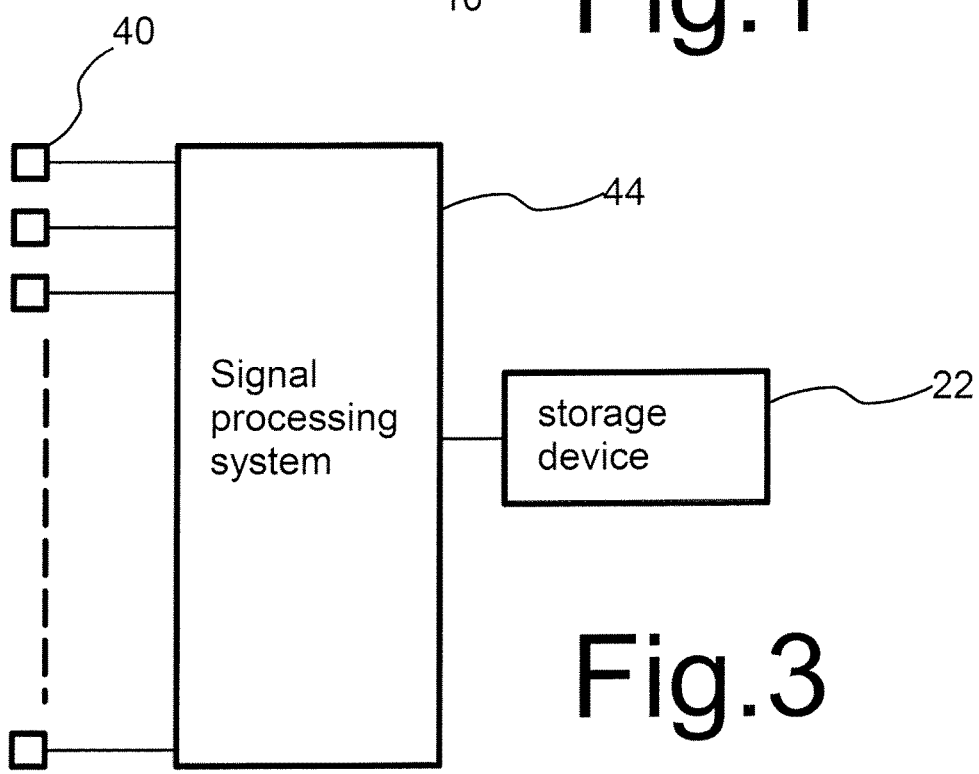
FIG. 3 shows a schematic of an ultrasound inspection system

FIG. 3 shows a schematic of an ultrasound inspection system comprising a plurality of ultrasound transducers 40, a signal processing system 44 and a storage device 22. Signal processing system 44 is coupled to ultrasound transducers 40, and storage device 22. The ultrasound inspection system may be part of a PIG (not shown). Ultrasound transducers 40 are located at respective different circumferential locations with respect to a central axis. Although transducers 40 are shown that each function both as transmitters and receiver, it should be appreciated that alternatively separate ultrasound transmitters and receivers may be used, for example alternately along a ring.

In operation, the ultrasound inspection system, or at least its transducers (receivers and transmitters) are moved through a pipe along an axial direction of the pipe, with the central axis of the ultrasound inspection system parallel to the axial direction of the pipe. Signal processing system 44 estimates distances of the transducers 40 to the inner surface of the wall of the pipe as a function of circumferential position, and causes ultrasound transducers 40 to transmit ultrasound pulses with relative delays according to differences between the estimated distances. Signal processing system 44 receives signals from transducers 40 in response to reception of ultrasound reflection of the transmitted ultrasound signals and processes these signals to estimate basic frequencies of response peaks in the spectral domain. Signal processing system 44 records results in storage device 46.

Figure 4:
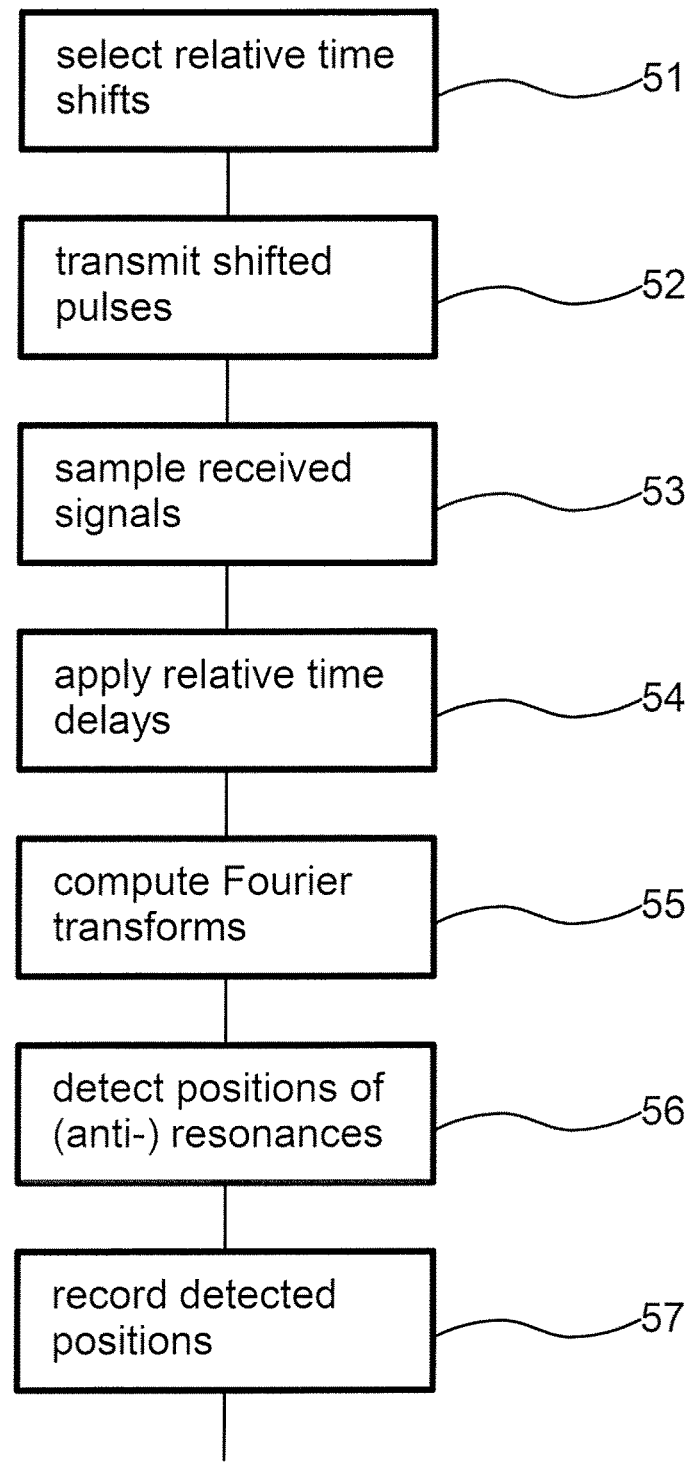
FIG. 4 shows a flow-chart of ultrasound inspection

FIG. 4 shows a flow-chart of operation of the ultrasound inspection system. In a first step 51, signal processing system 44 selects relative time shifts dt(m) to be applied to transmission of pulses from different transducers (labeled "m"). As will be discussed, the relative time shifts dt(m) may be used to apply a compensation for deformation of the pipe, so as to reduce contributions of shear modes in the pipe wall. Shear mode excitation can be reduced by providing wave fronts that are parallel to the inner surface of the pipeline wall. It has been found that in practical pipeline inspection, especially of pipelines that have been used for a considerable amount of time, a compensation for deviations of the shape from a circular cross-section is desirable to make defect monitoring more reliable.

In a second step 52, signal processing system 44 causes ultrasound transducers 40 to transmit time shifted ultrasound pulses $P(t;m)=P0(t-dt(m))$, using similar basic time dependent pulses P0 and imparting relative time shifts dt(m) to the pulses as a function of circumferential position of the ultrasound transducers 40 to correct for travel time differences from the different transducers to the inner surface of the pipe wall. In a third step 53, signal processing system 44 samples received signals S(t;m) from ultrasound transducers 40 following transmission of the pulses.

In a fourth step 54, signal processing system 44 applies relative time delays dt(m) to the received signals: $S'(t;m)=S(t-dt(m);m)$, in correspondence with the selected time shifts to correct for travel time differences from the inner surface of the pipe wall to the different transducers. In a fifth step 55, signal processing system 44 computes temporal Fourier transforms of the corrected signals.

In a sixth step 56, signal processing system 44 detects positions of (anti-)resonances in the amplitude of the Fourier transforms as a function of frequency for each of the transducers. In an embodiment, the location of the resonances and/or anti-resonances is detected by computing the size of the derivative of the phase of the Fourier transform with respect to the frequency and detecting peaks in this size as a function of frequency, optionally subject to an additional detection condition that the peak value exceeds a predetermined threshold.

It has been found that the size of the derivative of the phase of the Fourier transform detects mainly, if not only anti-resonances, because peaks in the size of the derivative are more pronounced for anti-resonances than for resonances. It has been found that use of anti-resonances makes it possible to obtain more reliable results. Optionally, the variation of the directions variation of the derivative before and after the peaks may be used to eliminate remaining detections of anti-resonances.

Alternatively, (anti-)resonances may be detected from the frequencies of peaks or dips in the amplitude of the Fourier transform. Compared to detection of anti-resonances from dips in the amplitude of the Fourier transform, use of the derivative of the phase has the advantage that there is less risk that the reduction in amplitude due to the deposits can lead to false detections, because the phase change that accompanies the reduction of the amplitude as a function of frequency due to the deposit is much more gradual than that due to anti-resonances.

In a seventh step 57, signal processing system 44 records the detected positions of the (anti-)resonances in storage device 46 in association with an indication of the axial position in the pipeline at which the signals were received. Subsequently, the recorded data may be used to control display of measured pipe thickness based on the distance between the (anti-)resonances and/or evaluation of absence of defects in the pipeline.

Alternatively, signal processing system 44 may be configured to detect whether the detected positions of lowest frequency peaks, and/or a frequency distance between detected successive frequencies of peak positions, are within a predetermined range corresponding to a required pipe wall thickness. Signal processing system 44 may be configured to generate alarm signals for those circumferential positions where the frequencies are not within the predetermined range. Determination whether a value is in a predetermined range may correspond to comparison with a threshold when the range extends unbounded from a minimum or maximum frequency upward or downward. Although an embodiment is shown where the results are recorded, in addition or alternatively signal processing system 44 may transmit the results to an external system and/or storage device 46 may be a part of the system that does not travel on the PIG.

Optionally, signal processing system 44 may perform an additional step (not shown) to compute reflection values for individual locations between the inner and outer surface of the pipe wall. In this additional step Stolt migration may be used, that is, for each individual location a sum of time shifted versions of received signals from different transducers may be computed, with time shifts that compensate for travel time differences from the individual locations to the different transducers, given the speed of sound in the inners space of the pipe and in the pipe wall. The sum may be a weighted sum. In an embodiment the sum may be computed over time shifted versions of received signals of a subset of the transmitters in a circumferential sector that includes the direction to the individual location. The sum of time shifted versions of received signals for an individual location in the pipe wall effectively provides the received signal for a synthetic receiver that is focused at the individual location. The sums of time shifted versions of received signals for different individual location in the pipe wall provide an image of the interior of the pipe wall wherein diffraction effects are reduced. This makes it possible to detect defect in the pipe wall more reliably.

As has been discussed, the application of a compensation for deformation of the pipe from a circular cross-section, by selecting the relative time shifts dt(m) in first step 51 can be used to make defect monitoring more reliable. Preferably, the selection of the time shifts is performed adaptively, dependent on measurements obtained when the PIG is in the pipeline during inspection. In an embodiment, the compensation may also be adapted to the mismatch between the position and orientation of the central axis of the array of transducers and the central axis of the pipe.

Figure 5:
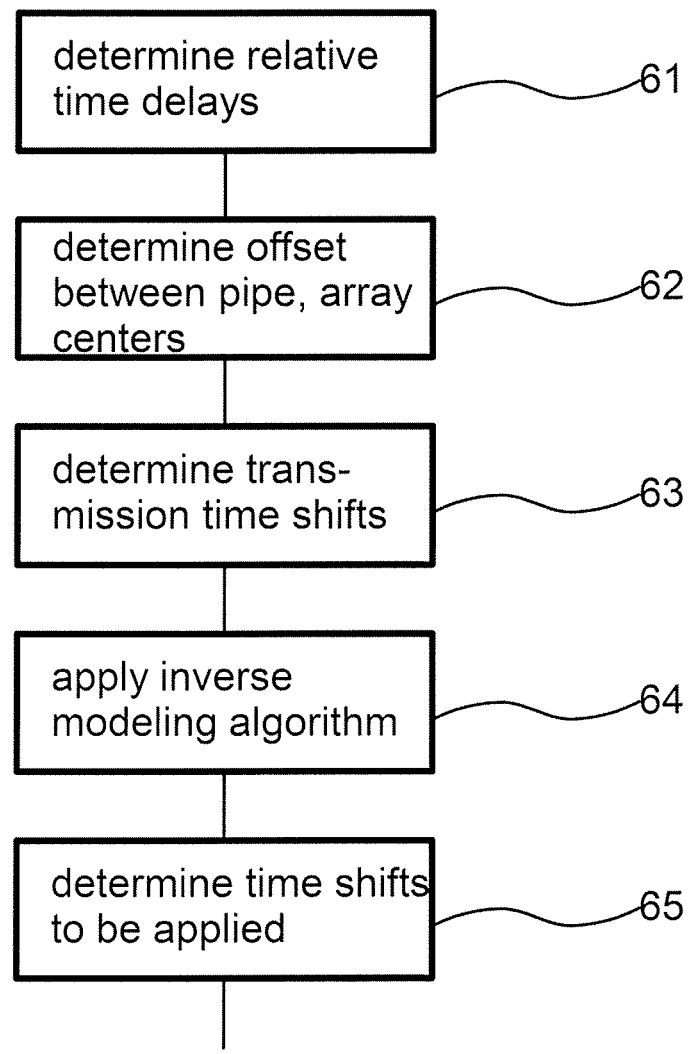
FIG. 5 shows a flow-chart of detected signal processing

FIG. 5 shows a detailed flow chart of an embodiment of adaptive time shift selection for use in first step 51 of the process of FIG. 4. In this embodiment measurements obtained using ultrasound pulses are used to select the relative time shifts. By way of example, a correction will first be described that assumes that the pipe cross-section has elliptical shape, with a priori unknown ellipticity and orientation of the longest axis of the ellipse. Parameters represent the ellipticity and the orientation of the longest axis. But the same type of computation may be performed for other shapes that are anisotropic for possible values of the parameters. The use of a model expressed in terms of parameters that affect a plurality of locations and preferably all locations along the represented surface has the advantage that a local defect will not result in a delay compensation that makes this defect invisible for detection.

In a first step 61, signal processing system 44 determines the relative time delays $T0(m)$ of the first reflection (due to reflection from the inner surface of the pipe wall) for each of the transducers (labeled by m).

In an embodiment, signal processing system 44 executes first step 61 by causing ultrasound transducers 40 to transmit ultrasound pulses simultaneously, recording the ultrasound response signals received by transducers 42, detecting the earliest reflection peaks in the amplitude of received responses for each of transducer 42 and determining the time delay $T0(m)$ between reception of this peak at a transducer labeled "m" and transmission of the pulses by ultrasound transducers 40.

In a further embodiment, the earliest reflection peaks and their position may be determined by cross-correlating the received signal at each transducer with a reference signal for that transducer (effectively obtaining values of the time integral of the product of the received signal and time shifted versions of the reference signal for a plurality of different time shifts, although the correlation may be computed in the Fourier transform domain) and determining the time delay from the time shift that results in maximum correlation. For this further embodiment, the reference signals may be signals obtained previously, when the transducers were located in a reference pipe.

In a second step 62, signal processing system 44 determines the offset between a center of the array of transducers 42 and a center of the pipe. The offset may be determined from the time delays $T0(m)$. In an embodiment, this comprises computing selecting, for each transducer m a two dimensional delay vector $(Tx(m), Ty(m))$ of reflection and taking the average $(<Tx>, <Ty>)$ of these two dimensional vectors of the different transducers. In an embodiment the two dimensional vector may be selected as a vector with a length $T0(m)$ and a direction corresponding to the direction of the position of the transducer m from the center of the array of transducers. That is, if the transducer m is located at a circumferential angle p(m), the two dimensional extrapolated position may be selected as $Tx(m)=T0(m)*\cos(p(m))$ and $Ty(m)=T0(m)*\sin(p(m))$.

In a third step 63, signal processing system 44 determines the transmission time shifts for the transducers. In an embodiment, the correction dT(m) is determined as the amplitude of a vector with components $(Tx(m)-<Tx>)/2$ and $(Ty(m)-<Ty>)/2$. This has been found to work for compensation of eccentric location of the PIG.

In a fourth step 64, signal processing system 44 applies an inverse modeling algorithm to the measured time delays $T0(m)$ to determine one or more parameters of the shape of the cross-section of the pipe in the plane of the sensing array (here cross-sections that differ only by a rotation are also referred to as having different shapes). In the illustrated embodiment of an elliptical shape, the parameters are the ratio between the size of its minor and major axis and direction of the major axis of the ellipse.

Inverse modeling algorithms are known per se. As is known per se, inverse modeling is a process that determines parameters of a forward model from measured values, in this case the time delays $T0(m)$. The forward model notionally defines a function F(m; parameters) which expresses predicted values of a measured variable, in this case time delays T0(m) for different transducers "m", dependent on the values of a set of parameters. In an example these parameters are the direction of the major axis of the ellipse, the sizes of its minor and major axis and optionally the location of its center. In an approximation the forward model defines F(m; parameters) as twice the distance between the location of the transducer "m" and the point of intersection of a radius from the center of the array of transducers through that location and the inner surface of the pipe wall. Preferably, distances expressed in terms of time units are used, that is, real distances divided by the speed of sound in the space within the pipe, which is assumed to be position independent.

An inverse modeling algorithm determines values of the parameters from the measured values of the variables for the locations "m". A probabilistic estimate may be used for this determination, based for example on a Bayesian model, which provides a probability distribution of the parameters given the measured values of the variables derived from an expression for the probability distribution of measured values of the variables given values of the parameters. For example, the inverse modeling algorithm may produce the values of the parameters where the probability distribution of the parameters has the highest likelihood.

One example of such an inverse modeling algorithm is a fitting algorithm, in which signal processing system 44 performs a search for parameter values at which a least square error between the predicted values and the measured values assumes its lowest value (this corresponds to maximum likelihood of a probability distribution that assumes a normal distribution for the measured values centered around the predictions F(m; parameters)). In an embodiment an a priori probability distribution of the values of the parameters may be used in the inverse modeling algorithm. A normal distribution centered around a priori reference parameter values may be used for example. Parameter values obtained for a previous axial position may be used as a priori reference values for example. In an embodiment, signal processing system 44 may be configured to detect transitions between successive sections of the pipeline (e.g. from ultrasound reflections from welding), and reset the a priori probability distribution to a wider a priori probability distribution for the first axial location after such a transition. As is known per se, in a Bayesian model the priori probability distribution can be used to define the a posteriori distribution from which the parameters are estimated. In the fitting algorithm this corresponds to signal processing system 44 searching for parameter values at which the least square error plus a term proportional to the square of the deviation from the newly estimated parameter values and the a priori reference values.

Although the example of determination of parameters of an ellipse has been described by way of example, it should be appreciated that alternatively parameters of other shapes may be used. For example, parameters may be used that define a base delay A and factors Bx, By of terms proportional to the sine and cosine function of the circumferential direction angle(m) of a transducer from the center of the array of transducers. For example:

$$F(m;A,Bx,By)=A+Bx*\cos(2*\text{angle}(m))+By*\sin(2*\text{angle}(m))$$

Equivalently, the factors Bx and By can be represented as an amplitude and phase angle of a vector with Bx and By as components. In further embodiments phase and amplitude of higher angular harmonics may be used.

Although fourth step 64 is shown in combination with second and third step 62, 63, it should be noted that these steps may be replaced with a single inverse modeling step, wherein signal processing system 44 determines the location of the center using the location as a parameter of the forward model in combination with the other parameters of the ellipse. For example, a model dependent on parameters A; Cx, Cy, Bx, By may be used, wherein Cx and Cy correspond to delay due to eccentricity of the center $$F(m;A,Cx,Cy,Bx,By)=A+Cx*\cos(\text{angle}(m))+Cy*\sin(\text{angle}(m))+Bx*\cos(2*\text{angle}(m))+By*\sin(2*\text{angle}(m))$$

In other embodiments the shape may be selected dependent on knowledge of the pipe structure. For example, it is known that the pipe consists of a bent sheet of which opposite edges have been welded together, a model may be used that has the circumferential position of the weld and an angle between the sheet ends that meet at the welds as parameters. Such a model may define that, in the cross-section perpendicular to the axial direction of the pipe, the sheet has a variable radius of curvature. In this embodiment, the circumferential position of the weld relative to the axis of the array of transducers and the angle at the weld, and optionally parameters that describe the curvature variation, may be determined by inverse modeling. For example the model may assume a predetermined pattern of variation of the curvature as a function of position along the circumference with the amplitude of the pattern as parameters (e.g. a radius of curvature $A*(1-\cos(2*PI*x/L))$ wherein A is an amplitude parameter, L is the width of the sheet from edge to edge and z is the position between the sheets). In this case the angle and the amplitude A are equivalent parameters. In a more refined model, one or more further parameters may be used that represents the shape of the radius of curvature as a function of position along the circumference.

Similarly, if it is known that the pipe is made from a sheet that has been helically wound, with welds between successive turns, a model with similar parameters may be used. In other embodiments a model may be used wherein the circumference of the pipe is a regular polygon with a given number of corners, with the location of one corner as a parameter.

In a fifth step 65, signal processing system 44 determines the time shifts dt(m) to be applied to the different transducers based on the parameter values obtained by inverse modeling. The time shifts are selected so as to approximate an incident wave front at the inner surface of the wall of the pipe that is parallel to the inner surface. In a first approximation, dt(m)=D+F(m; parameters)/2 may be used where D is an arbitrary value that is the same for all transducers, that is, the time shift is half the delay F(m; parameters) predicted by the forward model for the estimated values of the parameters. In other words, this will cause to move the transmission to an earlier time by half the delay predicted for the transducer m.

Although an embodiment has been described wherein it is assumed that signal processing system 44 uses the same model, possibly with different parameter values for all axial locations, it should be appreciated that alternatively, signal processing system 44 may be configured to switch between different models. In an example processing system 44 may be provided with data describing one or more predetermined cross-sections for special axial positions in the pipeline, in addition to the earlier described models for positions where the pipeline has axial translation symmetry. Data describing one or more predetermined cross-sections in bends in the pipeline may be provided for example and/or for locations where the pipeline is supported by special structures from the outside.

In this case processing system 44 may be configured to switch to using the data for one of the predetermined cross-sections at such special axial positions. Processing system 44 may be configured to do so when a detector (e.g. a detector (not shown) that mechanically senses diameter variations) detects such a special axial position. Alternatively, processing system 44 may be configured to compute score values for matches between predictions based on the different models and select the model with the best match score. Thus, processing system 44 may switch to a model for a bend when that best fits the measurements.

When processing system 44 switches to a model for data describing a predetermined cross-section for special axial positions in the pipeline, this data specify the time shifts dt(m) provided in first step 51 directly, or it may be used to derive these time shifts without further adaptation. In a further embodiment, processing system 44 may be configured to determine one or more parameters to adapt the pipe cross-section defined by the data for the special axial position. The parameters may include a rotation angle indicating a circumferential rotation of the pipe cross-section defined by the data, and/or a deformation parameter.

Although an embodiment has been described wherein transducers are used, i.e. wherein each transducer functions as a transmitter and receiver at the same location, it should be noted that alternatively transmitters and receivers located at different locations may be used. In this embodiment, a forward model may be used that accounts for the different locations. In an approximation, the interpolated delays may be associated with the transmitters, obtained by interpolating delays T0(m) measured for surrounding receivers. In this approximation, the transmitters can be treated similarly as the transducers in the described embodiment.

As described, all transducers (transmitters) are used to transmit pulses collectively, that is at the same time, or at times derived from a single time by applying the relative time shifts. This has the advantage that single transmissions suffice to determine the shape of the inner surface of the pipe wall and to detect defects. However, it should be noted that alternatively groups of part of the transducers (transmitters) along circle sectors of the circular array of transducers (transmitters) may used, wherein each time the transducers (transmitters) from the group transmit pulses collectively. For example, a first pulse may be transmitted from the transducers in a first semi-circle, followed by transmission from a second semi circle opposite to the first semi-circle, and optionally combined with pulses from the transducers in other semi-circles that overlap with the first and second semi-circle. Groups from circle sectors smaller than semi-circles may be used similarly. When a group in a sector that does not contain transducers along the full circle is used, at least for transducers (transmitters) m away from the edges of the sector useful delay measurements T0(m) and defect inspection can be obtained.

Processing system 44 may be a programmable computer with a program of instructions to cause the signal processing system to cause the described method. The instructions may be stored on a machine readable disk such as a magnetic or optical disk, or in a semi-conductor memory, e.g. a non-volatile memory. Processing system 44 may comprise a processor for executing all of the instructions or a plurality of cooperating processors that execute instructions of respective parts of the program.

Although a preferred embodiment has been shown wherein the transducers are arranged along a circle or, if separate transmitters and receivers are used, wherein the transmitters and receivers are arranged along a circle, in an embodiment with equally spaced transducers or transmitters and receivers, it should be realized that such arrangements are not indispensible. It suffices that transducers or transmitters and receivers are provided distributed over different radial directions from the center of the array, not necessarily at the same distance or at evenly spaced radial directions. The time shifts can be used to compensate for variation in the distance and uneven spacing only affects resolution.

The invention claimed is:

1. A method of ultrasound inspection of a hollow structure using an array of ultrasound transmitters located within the hollow structure distributed over different radial directions from a center of the array, the method comprising:

determining one or more parameters defining a shape and/or orientation of that shape of an inner surface of a wall of the hollow structure based on measured delays, measured between transmission of ultrasound pulses from the transmitters to reception of earliest received reflections of the ultrasound pulses;

computing time delays for respective ones of the transmitters along at least a sector of the array to compensate for estimated differences between travel times from the transmitters to the shape defined by the one or more parameters;

transmitting ultrasound waves to form a wave front composed of joint transmissions from the transmitters along at least said sector of the array, with the relative time delays between waves transmitted by the respective ones of the transmitters; and detecting reflections of the joint transmissions by computing derivatives with respect to frequency of phase values of Fourier transforms of the reflections.

2. A method according to claim 1, wherein the hollow structure is a pipeline, and wherein said one or more parameters define the shape and/or orientation of an elliptically shaped cross-section of the inner wall surface, a polygonal shaped cross-section, and/or a curved shaped cross-section part, the curved shaped cross-section part having ends meeting at an angle described by the one or more parameters.

3. A method according to claim 1, wherein the reflections are detected by detecting peaks in the size of the computed derivatives of the phase values.

4. A method according to claim 3, comprising determining a lowest frequency at which a peak has been detected, and/or distance between detected successive peaks, and determining whether the lowest frequency and/or distance lies within a predetermined range.

5. A method according to claim 1, wherein reflected signals of the jointly transmitted ultrasound waves are received at an array of receivers, and the reflected signal received at each of the respective ones of the receivers in the array is time shifted to compensate for an estimated difference between travel times to the respective one of the receivers, the estimation of the difference between travel times being based on the shape defined by the one or more parameters.

6. A method according to claim 1, comprising inspection of defects at intermediate locations between the inner and outer surface of the wall of the hollow structure, wherein reflected signals of the jointly transmitted ultrasound waves are received at an array of receivers, and wherein for each of said intermediate locations the reflected signals are time shifted to compensate for estimated travel time differences to and from the intermediate locations, dependent on the shape defined by the parameters.

7. A method according to claim 1, wherein the ultrasound pulses are transmitted simultaneously from the transmitters along at least said sector of the array, and the delays between reception of the transmitted ultrasound pulses are detecting by correlating predetermined reference signals with measured signals received in response to the transmitted ultrasound pulses.

8. A tangible computer readable medium comprising instructions for a programmable signal processing system that, when executed by the programmable signal processing system will cause the programmable signal processing system to execute the method of any one of the preceding claims to be executed.

9. A system for ultrasound inspection of a hollow structure, the system comprising
 a carrier;
 an array of ultrasound transmitters and receivers, or transducers operable both as transmitters and receivers, mounted on the carrier, distributed over different radial directions from a center of the array;
 a processing system configured to;
 determine one or more parameters defining a shape and/or orientation of that shape of an inner surface of a wall of the hollow structure based on measured delays, measured between transmission of ultrasound pulses from the transmitters to reception of first reflections of the ultrasound pulses;
 compute time delays for respective ones of the transmitters along at least a sector of the array to compensate for estimated differences between travel times from the transmitters to the shape defined by the one or more parameters;
 cause the transmitters to transmit ultrasound waves forming a wave front composed of joint transmissions from the transmitters along at least the sector of the array, with the computed time delays between waves transmitted by the respective ones of the transmitters; and
 process reflections of the joint transmissions received at the receivers by computing derivatives with respect to frequency of phase values of Fourier transforms of the reflections.

10. A system according to claim 9, wherein the processing system is configured to use one or more parameters that define the shape and/or orientation of an elliptically shaped cross-section of the inner wall surface, a polygonal shaped cross-section, and/or a curved shaped cross-section part, the curved shaped cross-section part having ends meeting at an angle described by the one or more parameters.

11. A system according to claim 9, wherein the processing system is configured to detect the reflections by detecting peaks in the size of the computed derivatives of the phase values.

12. A system according to claim 11, wherein the processing system is configured to determine a lowest frequency at which a peak has been detected, and/or frequency distance between detected successive peaks, and determining whether the lowest frequency and/or distance lies within a predetermined range.

13. A system according to claim 9, wherein the processing system is configured to receive reflected signals of the jointly transmitted ultrasound waves from the receivers, and to apply to the time shifts the reflected signals to compensate for estimated differences between travel times to different receiver from the shape defined by the one or more parameters.

14. A system according to claim 9 for inspection of defects at intermediate locations between the inner and outer surface of the wall of the hollow structure, wherein the processing system is configured to receive reflected signals of the jointly transmitted ultrasound waves from the receivers, and, for each of said intermediate locations the reflected signals being applied to a time shift to compensate for estimated travel time differences to and from the intermediate locations, dependent on the shape defined by the parameters.

15. A system according to claim 9, wherein the processing system is configured to cause the transmitters to transmit the ultrasound pulses simultaneously from the transmitters along at least said sector of the array, and to detect the delays between reception of the transmitted ultrasound pulses by correlating predetermined reference signals with measured signals received in response to the transmitted ultrasound pulses.

16. A method of ultrasound inspection of a hollow structure using an array of ultrasound transmitters located within the hollow structure distributed over different radial directions from a center of the array, the method comprising:
 determining one or more parameters defining a shape and/or orientation of that shape of an inner surface of a wall of the hollow structure based on measured delays, measured between transmission of ultrasound pulses from the transmitters to reception of earliest received reflections of the ultrasound pulses;
 computing time delays for respective ones of the transmitters along at least a sector of the array to compensate for estimated differences between travel times from the transmitters to the shape defined by the one or more parameters;
 transmitting ultrasound waves to form a wave front composed of joint transmissions from the transmitters along at least said sector of the array, with the relative time delays between waves transmitted by the respective ones of the transmitters; and
 detecting reflections of the joint transmissions by detecting positions of resonances and/or anti-resonances from frequencies of peaks or dips in an amplitude of Fourier transforms of the reflections.

17. A system for ultrasound inspection of a hollow structure, the system comprising
 a carrier;
 an array of ultrasound transmitters and receivers, or transducers operable both as transmitters and receivers, mounted on the carrier, distributed over different radial directions from a center of the array;
 a processing system configured to;
 determine one or more parameters defining a shape and/or orientation of that shape of an inner surface of a wall of the hollow structure based on measured delays, measured between transmission of ultrasound pulses from the transmitters to reception of first reflections of the ultrasound pulses;
 compute time delays for respective ones of the transmitters along at least a sector of the array to compensate for estimated differences between travel times from the transmitters to the shape defined by the one or more parameters;
 cause the transmitters to transmit ultrasound waves forming a wave front composed of joint transmissions from the transmitters along at least a sector of the array, with the computed relative time delays between waves transmitted by the respective ones of the transmitters; and process reflections of the joint transmissions received at the receivers by detecting positions of resonances and/or anti-resonances from frequencies of peaks or dips in an amplitude of Fourier transforms of the reflections.

\* \* \* \* \*